United States Patent [19]

Knott et al.

[11] Patent Number: 5,622,722
[45] Date of Patent: Apr. 22, 1997

[54] SPHEROID FORMULATION

[75] Inventors: Trevor J. Knott, Wickford; Sandra T. A. Malkowska, Cambridge; Philip J. Neale, Cambridge; Stewart T. Leslie, Cambridge, all of United Kingdom; Ronald B. Miller, Basel, Switzerland; Derek A. Prater, Cambridge, United Kingdom

[73] Assignee: Euro-Celtique, S.A., Luxembourg

[21] Appl. No.: 349,556

[22] Filed: Dec. 5, 1994

Related U.S. Application Data

[63] Continuation of Ser. No. 20,142, Feb. 19, 1993, abandoned.

[30] Foreign Application Priority Data

Feb. 20, 1992 [GB] United Kingdom ............... 9203689

[51] Int. Cl.$^6$ ........................... A61K 9/36; A61K 9/16
[52] U.S. Cl. .......................................... 424/494
[58] Field of Search ........................ 424/461, 489, 424/493, 494; 514/781

[56] References Cited

U.S. PATENT DOCUMENTS

| | | | |
|---|---|---|---|
| 4,867,785 | 9/1989 | Heafield et al. | 424/461 |
| 4,990,341 | 2/1991 | Goldie et al. | 424/484 |
| 5,049,394 | 9/1991 | Howard et al. | 424/490 |
| 5,350,584 | 9/1994 | McClelland et al. | 424/78.1 |

FOREIGN PATENT DOCUMENTS

| | | |
|---|---|---|
| 0231026 | 8/1987 | European Pat. Off. . |
| 0237506 | 9/1987 | European Pat. Off. . |
| 0452862 | 10/1991 | European Pat. Off. . |
| 1390311 | 4/1975 | United Kingdom . |
| 2189700 | 11/1987 | United Kingdom . |

*Primary Examiner*—Peter F. Kulkosky
*Attorney, Agent, or Firm*—Steinberg, Raskin & Davidson, P.C.

[57] ABSTRACT

A pharmaceutical composition comprising spheroids comprising a water-soluble active ingredient or a pharmaceutically acceptable salt thereof, microcrystalline cellulose and a sugar. Preferably the active ingredient is hydromorphone hydrochloride and the sugar is lactose. Surprisingly the incorporation of a sugar improves the dissolution rate of the spheroid formulation instead of reducing the dissolution rate by competing with the active ingredient for solubilization.

9 Claims, No Drawings

SPHEROID FORMULATION

This is a continuation of application Ser. No. 08/020,142, filed Feb. 19, 1993, now abandoned.

BACKGROUND OF THE INVENTION

In the pharmaceutical art water-soluble active ingredients are conventionally formulated together with insoluble excipients in an attempt to maximize their dissolution rate. One such non water soluble pharmaceutical excipient which is widely used is microcrystalline cellulose. Microcrystalline cellulose is particularly useful in the formation of spheroids by spheronization and can itself be processed to give spheroids by simple granulation with water followed by extrusion and spheronization. In general, the greater the proportion of microcrystalline cellulose present in a pharmaceutical composition, the easier it is to form spheroids.

Microcrystalline cellulose as an excipient generally exercises little control over the release of active ingredient from a dosage form and it would therefore be expected that compositions containing a high proportion of microcrystalline cellulose would show normal release characteristics.

A normal release pharmaceutical preparation is one that achieves fast release of active ingredient in a short period of time. Conventionally a dissolution rate of 90% or more in 45 minutes would be acceptable to constitute a normal release preparation.

SUMMARY OF THE INVENTION

We have found that capsules containing spheroids comprising hydromorphone hydrochloride and a high level of microcrystalline cellulose exhibit an unacceptably slow release rate for a normal release preparation. As hydromorphone hydrochloride is highly water soluble this result is unexpected.

It is accordingly a primary eject of the present invention to provide a normal release spheroid formulation comprising both a water-soluble active ingredient and microcrystalline cellulose which overcomes the above problems.

With the above object in view, the present invention relates to a pharmaceutical composition for oral administration and to a process for its preparation. In particular the invention relates to a pharmaceutical composition comprising spheroids comprising a water-soluble active ingredient, microcrystalline cellulose and a sugar.

We have surprisingly found that the incorporation of a sugar improves the dissolution rate of the spheroid formulation with the microcrystalline cellulose. Conventionally it would be expected that such a soluble excipient would reduce the dissolution rate by competing with the active ingredient for solubilization in the dissolution media (as described, for example by Lerk et al, Journal of Pharmaceutical Sciences, 68(2), 205–210, (1979).

The present invention therefore provides a pharmaceutical spheroid composition comprising a water-soluble active ingredient or a pharmaceutically acceptable salt thereof, microcrystalline cellulose and a sugar.

The term "spheroid" is conventional in the pharmaceutical art and means a spherical granule having a diameter of between 0.1 mm and 2.5 mm, especially between 0.5 mm and 2 mm.

The water soluble active ingredient may suitably be any active ingredient that dissolves 1 part solute by weight in 30 parts or less of solvent. Suitable active ingredients for use according to the invention include (a) Analgesics such as codeine phosphate, codeine sulphate, dextropropoxyphene hydrochloride, dihydrocodeine tartrate, diamorphine hydrochloride, hydromorphone hydrochloride, methadone hydrochloride, morphine acetate, morphine hydrochloride, morphine sulphate, oxymorphone.

(b) Anti-emetics such as metoclopramide;

(c) Vasodilators such as diltiazem and naftidrofuryl oxalate;

(d) Xanthines such as aminophylline;

(e) Antihypertensive agents such as captopril, clonidine hydralazine and propranolol;

(f) Anti-arrhythmic agents such as disopyramide phosphate, mexiletine, procainamide, quinidine, tocainide and verapamil;

(g) Bronchodilators such as salbutamol, isoprenaline, fenoterol and terbutaline;

(h) Anthelmintics such as levamisole, tetramisole and diethylcarbamazine;

(i) Corticosteroids such as dexamethasone sodium phosphate, hydrocortisone sodium phosphate, hydrocortisone sodium succinate; and pharmaceutically acceptable salts thereof.

Preferably however the active ingredient is hydromorphone or a pharmaceutically acceptable salt thereof, particularly hydromorphone hydrochloride.

The composition according to the invention preferably contains from 0.1% to 25% by weight, more preferably from 0.5 to 10% by weight, especially from 1.0 to 5.0% by weight of the active ingredient.

The microcrystalline cellulose used may be, for example, Avicel pH 101 or Avicel pH 102 (Trade Marks, FMC Corporation). Preferably the composition according to the invention contains from 10 to 90% by weight, preferably 25 to 75% by weight of microcrystalline cellulose.

Suitable sugars for use according to the invention include water-soluble sugars such as sucrose, fructose, xylitol, sorbitol or preferably lactose. The composition according to the present invention preferably contains from 25 to 75% by weight, especially 40 to 60% by weight of the sugar, with reference to the remainder of the composition. According to one preferred embodiment of the present invention the weight ratio of the microcrystalline cellulose to the sugar is between 1:3 and 3:1, especially 1:1.

A particularly preferred composition according to the invention comprises spheroids comprising 1.0 to 5.0% by weight hydromorphone hydrochloride, 25 to 75% by weight microcrystalline cellulose and 40 to 60% by weight lactose.

In addition the spheroids according to the present invention may also contain suitable quantities of other materials such as binders, colorants and flavorants that are conventional in the pharmaceutical art. Suitable binders include low viscosity water soluble polymers, water soluble substituted cellulose ethers such as hydroxypropylmethyl cellulose being preferred.

According to a further aspect the present invention provides a process for preparing a spheroid formulation comprising (a) blending a mixture comprising a water soluble active ingredient or a pharmaceutically acceptable salt thereof, microcrystalline cellulose and a sugar;

(b) extruding the blended mixture to give an extrude;

(c) spheronising the extrudate until spheroids are formed; and (d) drying the spheroids.

Preferably the spheroids are dried until the moisture content is 7% by weight or less of the total spheroid weight as measured by Karl Fischer titration. Conveniently after drying the spheroids are sieved to give spheroids having a predetermined particle size range.

Compositions according to the present invention are conveniently formulated for oral administration in unit dosage form in conventional manner. A unit dose may consist of, for example, a capsule, sachet or cachet containing a predetermined quantity of the spheroids. It will be appreciated that the quantity is determined by the dose of active ingredient to be incorporated in a unit dose of the composition. Preferred doses will be well known to those skilled in the art.

Compositions in the form of a capsule or cachet may be administered directly via the oral route. A capsule or sachet may conveniently be sprinkled onto food to be taken as part of a meal.

DESCRIPTION OF PREFERRED EMBODIMENTS

The following examples are given to further illustrate the present invention. The scope of the invention is not to be limited, however, to the details of the examples.

Example 1

Capsules having the following formulation were prepared;

|   | mg |
| --- | --- |
| Hydromorphone hydrochloride | 1.3 |
| Microcrystalline cellulose Avicel pH 101 | 39.35 |
| Lactose, anhydrous | 39.35 |
| Purified Water | q.s. |
| Fill Weight | 80 |

Hydromorphone hydrochloride (1.3 mg), microcrystalline cellulose (39.35 mg) and lactose (39.35 mg) were dry mixed. Water was added to from a granular mass which was then extruded to form a uniform, free flowing extrudate. The extrudate was spheronized and the resultant spheroids dried until they had a moisture content of about 7% by weight. The dried spheroids were sieved to obtain the 0.85–1.4 mm sieve fraction.

Example 2

The procedure of Example 1 was followed except that the amount of hydromorphone hydrochloride was increased to 2.6 mg and that of microcrystalline cellulose and lactose to 78.7 mg. The fill weight was 160 mg.

Comparative

Following the procedure of Example 1 a composition having the following formulation was prepared;

|   | mg |
| --- | --- |
| Hydromorphone hydrochloride | 1.3 |
| Microcrystalline cellulose Avicel pH 101 | 77.0 |
| Hydroxypropylmethylcellulose, E15 | 1.7 |
| Purified Water | q.s. |
| Fill Weight | 80 |

The water soluble binder, hydroxypropylmethylcellulose, was included in the formulation to ensure that spheroids were produced with a low friability.

In Vitro Dissolution Studies

In vitro dissolution studies were conducted on compositions prepared as described in Examples 1–2 and the comparative example. The dissolution method was by Ph. Eur. paddle apparatus operated at 50 rpm with distilled water at 37° C. as dissolution media.

Results are given in Table 1. Table 1 also gives the results obtained with a marketed normal release hydromorphone hydrochloride tablet (DILAUDID, trade mark).

TABLE 1

| Time | | | wt % Hydromorphone released | |
| --- | --- | --- | --- | --- |
| (mins) | Ex 1 | Ex 2 | Comparative | Dilaudid ® |
| 10 | 79.7 | 83.3 | 52.7 | 59.4 |
| 20 | 90.5 | 93.3 | 69.2 | 88.6 |
| 30 | 90.7 | 96.7 | 73.3 | 100.8 |
| 45 | 93.6 | 99.1 | 77.9 | 103.1 |
| 60 | 94.0 | 101.2 | 85.7 | 103.1 |

While the invention has been illustration with respect to particular formulations, it is apparent that variations and modifications of the invention can be made without departing from the spirit and scope thereof.

We claim:

1. A normal release pharmaceutical spheroid composition, comprising about 0.1–25% by weight hydromorphone or a water soluble pharmaceutically acceptable salt thereof, microcrystalline cellulose and a sugar, the ratio of said microcrystalline cellulose to said sugar being between 1:3 and 3:1 by weight, said composition having a dissolution rate of 90% or more in 45 minutes, thus effecting normal release of said hydromorphone from said composition.

2. Composition according to claim 1, wherein the ratio of said microcrystalline cellulose to said sugar is 1:1.

3. Composition according to claim 1, wherein the microcrystalline cellulose is present in an amount of from about 25–75% by weight.

4. Composition according to claim 3, wherein the sugar is present in an amount of from about 25–75% by weight.

5. Composition according to claim 4, wherein the ratio of microcrystalline cellulose to sugar is between 1:3 and 3:1 by weight.

6. Composition according to claim 1, wherein the sugar is lactose.

7. Composition according to claim 1, wherein the spheroids contain between about 1–5% by weight hydromorphone hydrochloride, about 25–75% by weight microcrystalline cellulose, and about 40–60 by weight lactose.

8. Composition according to claim 1, in oral dosage form.

9. Method of producing the composition of claim 1, which comprises:

(a) blending a mixture of said water soluble active ingredient, microcrystalline cellulose and sugar and adding water to form a blending mixture, (b) extruding the blending mixture to form an extrudate, (c) spheroidizing the extrudate until spheroids are formed, and (d) drying the spheroids.

* * * * *